United States Patent [19]
Fuisz

[11] Patent Number: 4,778,459
[45] Date of Patent: Oct. 18, 1988

[54] HIGH ABSORBENCY DIAPER WITH COMPOSITE ABSORBENT LAYER

[76] Inventor: Richard C. Fuisz, 4146 Green Pond Rd., Bethlehem, Pa. 18017

[21] Appl. No.: 4,771

[22] Filed: Jan. 9, 1987

Related U.S. Application Data

[63] Continuation of Ser. No. 709,728, Mar. 8, 1985, abandoned.

[51] Int. Cl.[4] .............................................. A61F 13/16
[52] U.S. Cl. ................................. 604/378; 604/385.1
[58] Field of Search ............... 604/368, 369, 378, 379, 604/380, 385.1

[56] References Cited

U.S. PATENT DOCUMENTS

| | | | |
|---|---|---|---|
| 3,799,167 | 3/1974 | Miller et al. | 604/382 |
| 3,918,433 | 11/1975 | Fuisz | 128/760 |
| 4,029,100 | 6/1977 | Karami | 604/369 |
| 4,333,463 | 6/1982 | Holtman | 604/378 |
| 4,333,465 | 6/1982 | Wiegner | 604/366 |
| 4,413,996 | 11/1983 | Taylor | 604/382 |
| 4,490,147 | 12/1984 | Pierce et al. | 604/378 |
| 4,501,586 | 2/1985 | Holtman | 604/380 |

Primary Examiner—J. Yasko
Assistant Examiner—Sharon Rose
Attorney, Agent, or Firm—Brooks Haidt Haffner & Delahunty

[57] ABSTRACT

A disposable diaper contains an absorbent layer in which an island of highly absorbent material is located where it is surrounded by an expanse of lesser absorbent material that extends throughout the remainder of the diaper. A liquid impermeable panel or coated region diverts urine from the lesser absorbent material to the island material.

27 Claims, 3 Drawing Sheets

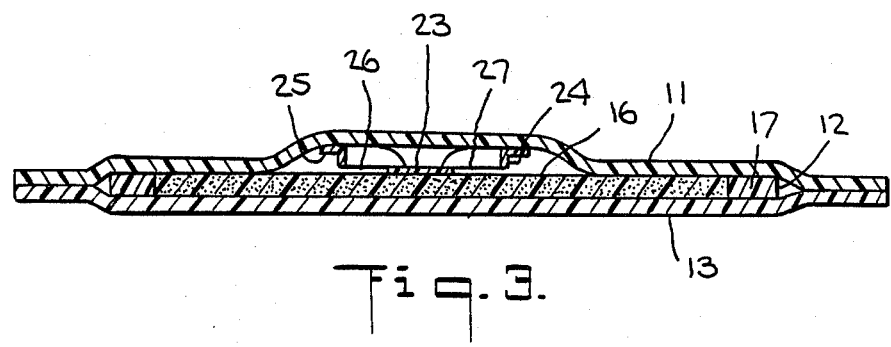
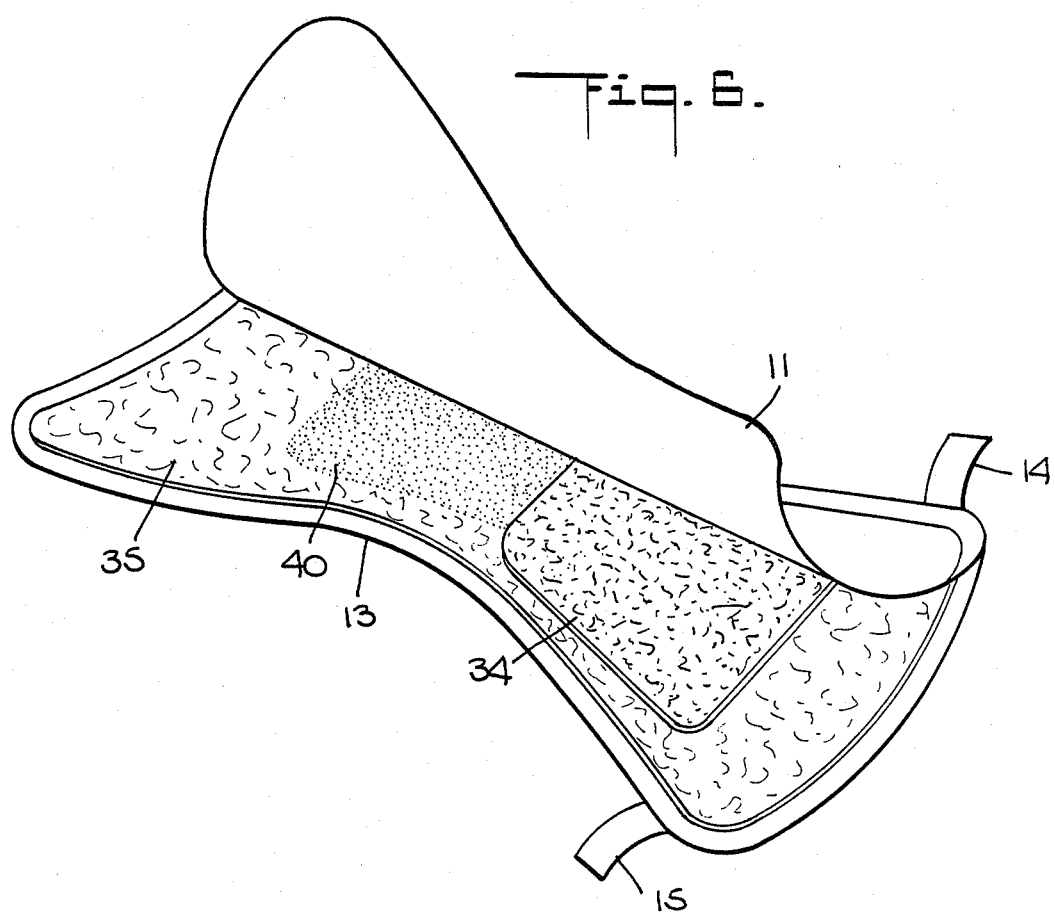

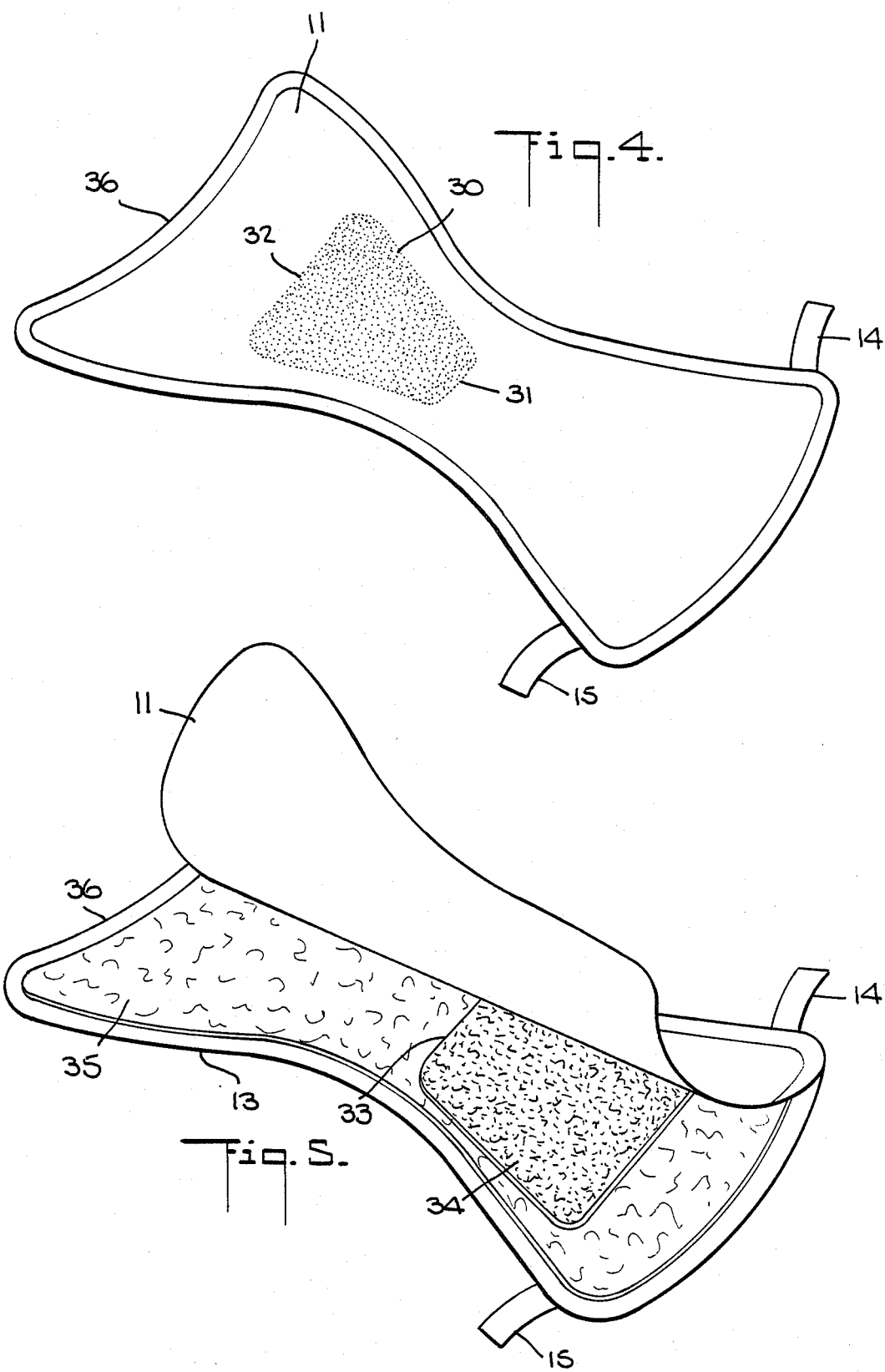

HIGH ABSORBENCY DIAPER WITH COMPOSITE ABSORBENT LAYER

This application is a continuation, of application Ser. No. 709,728, filed Mar. 8, 1985, now abandoned.

BACKGROUND OF THE INVENTION

The present invention relates to disposable diapers. More particularly, it relates to a diaper construction having increased absorbency over that found in anything known heretofore.

Disposable diapers are generally of multi-ply construction with those presently in use having an absorbent layer sandwiched between a liquid impermeable back or outer sheet and a porous top sheet. The patent literature describes these diapers as having a top sheet that is substantially porous and made completely or in part of synthetic fibers such as polyolefin, rayon or the like, or of natural fibers such as cotton. The fibers are typically bound together by a polymeric binder such as polyacrylate. The absorbent layer or core is described generally as being constructed from highly absorbent essentially hydrophilic fiber aggregates, and may consist of piles of creped cellulose wadding. Finally, the back sheet can be constructed from a thin plastic film of polyethylene, polypropylene or other flexible moisture impeding material which is substantially water impervious.

More specifically, the absorbent layer in heretofore known diaper construction has been fabricated from a multiplicity of piles of creped cellulose wadding, fluffed cellulosic fibers or wood pulp, the latter sometimes being referred to as airfelt, from textile fibers or other absorbent material. While the known diapers are quite satisfactory and have virtually supplanted the reusable cotton diaper, there remains considerable room for improvement. In particular, there is a need for an inexpensive, more absorbent and more comfortable diaper for infant wear.

In my prior pending application Ser. No. 644,442 filed Aug. 27, 1984, and entitled "Urine Collecting Device," the disclosure of which is incorporated herein by reference, there is described a collecting device in which a predetermined size and shape piece of dry compressed cellulose sponge is disposed within a compartment formed from plastic sheet material, the compartment being larger than the dry piece of sponge at least in the height or thickness direction, but smaller than the wet expanded piece of sponge at least in the thickness direction, so as to limit expansion of the sponge and thereby the amount of liquid which it absorbs to a predetermined quantity. The compartment has an opening in a side wall that communicates with a channel formed in a fan shaped panel of the plastic sheet material extending from the compartment, the channel being arranged to conduct urine to the opening when the device is attached to a diaper or other article of clothing, and worn with the panel adjacent the genitalia and the compartment adjacent the perineum.

SUMMARY OF THE INVENTION

With the above-mentioned background, it is an object of the present invention to provide a disposable diaper that is more absorbent than those known heretofore.

It is a further object to accomplish the foregoing objective in an economic manner.

In accordance with one aspect of the present invention, there is provided a disposable diaper comprising at least a layer of absorbent material extending throughout substantially the entire diaper, said absorbent layer being characterized by an island of a first absorbent material surrounded by an expanse of a second absorbent material, where the liquid absorbing capacity per unit volume of said island material is greater than that of said surrounding expanse.

From a more specific point of view, the disposable diaper comprises at least a layer of absorbent material having a surface intended to face the wearer and extending throughout substantially the entire diaper, said absorbent layer including an island of a first absorbent material surrounded by an expanse of a second absorbent material, where the liquid absorbing capacity per unit volume of said island material is greater than that of said surrounding expanse, said island being located in that portion of the diaper that, when the diaper is worn, places said island at the rear of the wearer extending toward the perineum region, and an expanse of liquid impermeable material overlying that portion of said second absorbent material expanse that overlies the general region of the genitalia when the diaper is worn, said expanse of impermeable material extending from said genitalia region to said island for diverting and directing urine away from said second absorbent material and toward said island of material, said expanse of impermeable material being constructed to permit urine access to said island material.

BRIEF DESCRIPTION OF THE DRAWINGS

The invention will be better understood after reading the following detailed description of the presently preferred embodiments thereof with reference to the appended drawings in which:

FIG. 3 is a traverse sectional view taken along the line 3—3 in FIG. 2;

FIG. 4 is a view similar to that of FIG. 1 but showing a modified embodiment of the invention;

FIG. 5 is a view similar to FIG. 4 but with the top sheet rolled partially back in order to reveal the interior construction; and FIG. 6 is a view similar to FIG. 5 but showing a modification thereof.

The same reference numerals are used throughout the drawings to designate the same or similar parts.

DETAILED DESCRIPTION OF THE PRESENTLY PREFERRED EMBODIMENTS

Figure 1:
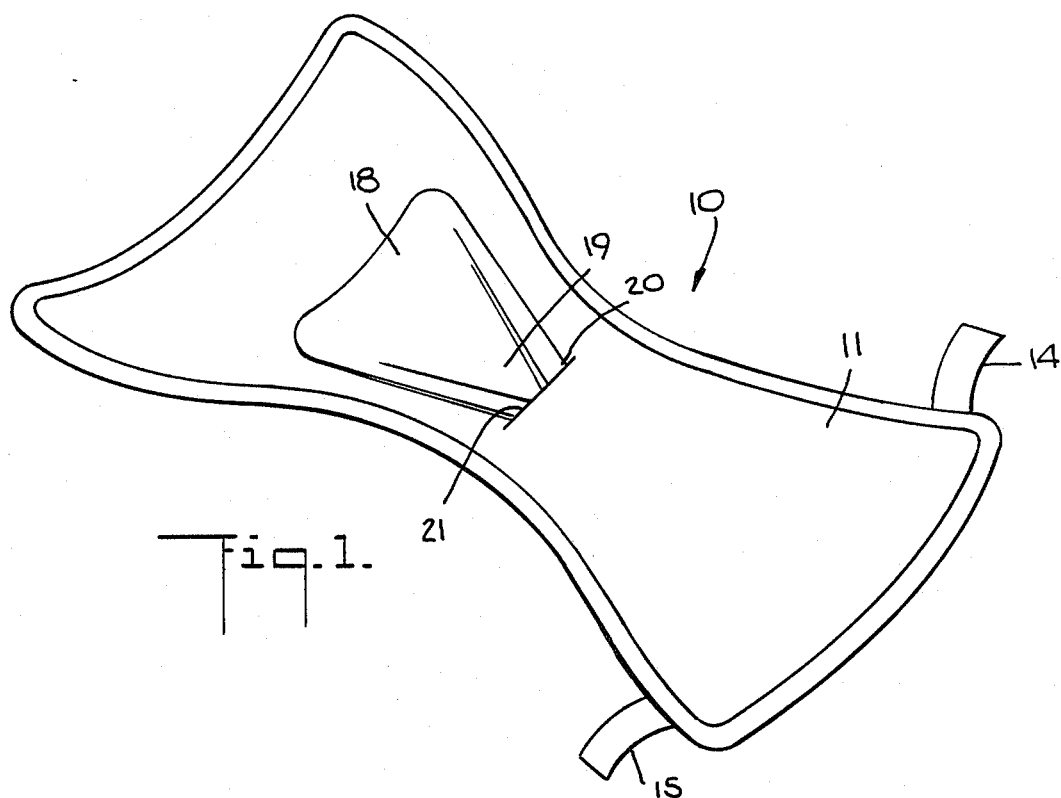
FIG. 1 is a perspective view of the top sheet side of a diaper embodying the present invention.
Figure 2:
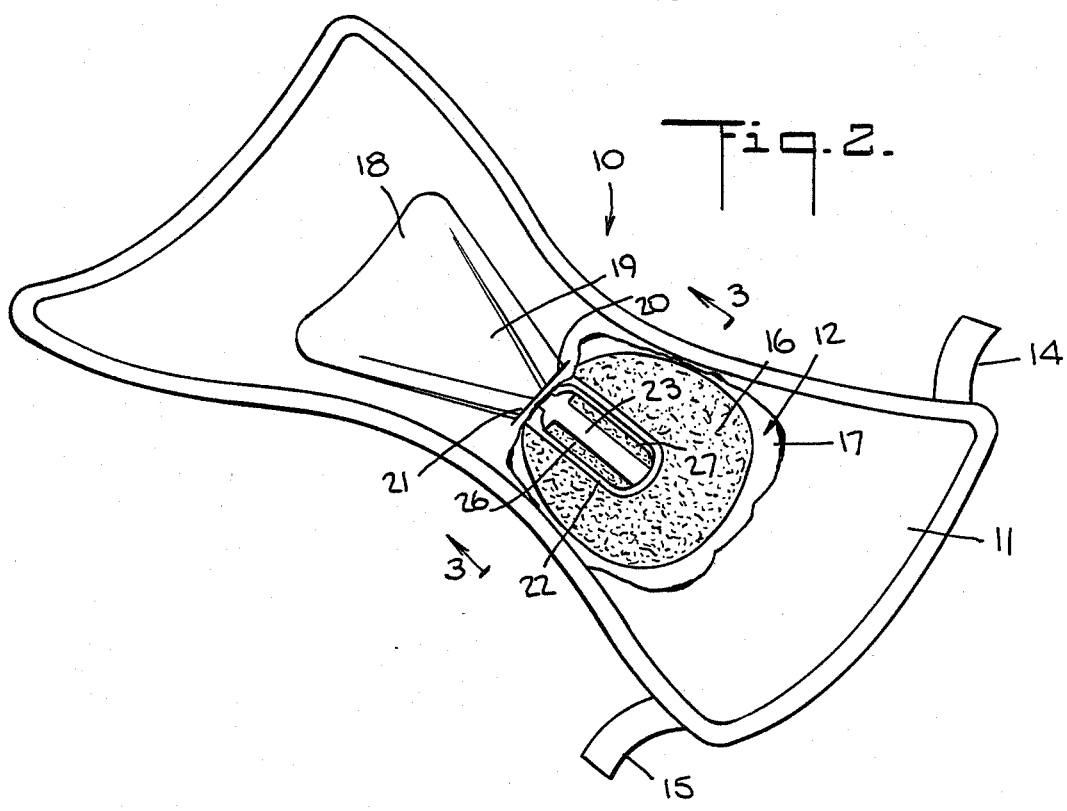
FIG. 2 is a view similar to FIG. 1, but with a portion broken away to reveal details of the internal construction.

Referring to FIGS. 1 to 3, there is illustrated by way of example one embodiment of the present invention. The reference numeral 10 designates generally a diaper having a top sheet 11, a layer of absorbent material 12, and a back sheet 13. The usual adhesive or fastening tabs 14 and 15 are shown appended to one end of the diaper 10. The top sheet 11 and the back sheet 13 may be formed from any of the materials presently conventionally used for this purpose. The important requirement is that the back sheet be impervious to liquid while the top sheet is porous.

The present invention deals primarily with the absorbent layer 12 that, in the embodiment being described, has an island 16 of a first absorbent material surrounded by an expanse 17 of another absorbent material. The absorbent material 17 may take any of the known forms of construction such as those enumerated above in the discussion of the background of the present invention. By virtue of the present invention, the material 17 may be selected with economic considerations of prime importance and absorbency considerations of only secondary importance. This follows from the fact that the island material 16 is intended to absorb the major portion of the urine excreted by the wearer. It is presently preferred that the quantity and nature of the material in the island 16 have the capacity of absorbing at least 50 cc. of urine. It has been found that a six inch diameter circle of highly compressed cellulose sponge as furnished by Americal Sponge and Chamois Co., Inc., of Long Island City, N.Y., and having a compressed thickness of no more than 1/16", is expandable to at least ⅜" in thickness and is capable of absorbing the stated quantity of urine. Such sponge as presently contemplated has a compressed volume of approximately 7 in$^3$, and is expandable to a volume of approximately 35 in$^3$ when completely wetted and relaxed. While the island of material 16 is illustrated in FIGS. 1 to 3 as being embedded in the surrounding expanse of material 17, the island 16 may be superimposed, if desired, on the surface of the material 17 such as shown in FIG. 5. Moreover, the configuration of the island 16 is not limited to the circular construction shown in FIG. 2, but may take any appropriate shape such as a rectangle approximately 4"×6" or it may take the form of a regular trapezoid such as that shown in FIG. 5.

Returning to FIGS. 1 to 3, it will be seen that the island of material 16 is located in that portion of the diaper 10 that when the diaper is worn places said island at the rear of the wearer extending toward the perineum region. For the purpose of diverting and directing urine away from the absorbent material 17 that extends throughout the general expanse of the diaper, and toward the island of material 16, there is provided an expanse of impermeable material overlying that portion of the absorbent material expanse that overlies the general region of the genitalia when the diaper is worn. In the present example, this impermeable expanse of material is shown as comprising a panel 18 including a channel 19 for guiding urine therealong. The panel 18 is shown as fan shaped and may be formed from a thin film or sheet of polyvinyl chloride resin.

As shown in FIG. 2, the panel 18 at its waist 20 extends through a slit 21 in the top sheet 11 where it takes on a generally rectangular configuration overlying the island 16. The rectangular extension of the panel 18 is designated generally by the numeral 22 and, as best seen in FIG. 3, has a depressed region 23 constituting essentially a longitudinal continuation of the bottom of the channel 19. This depressed region with side walls 24 and an encircling flange 25 lends structural strength to the rectangular section, the bottom of which has cutouts at 26 and 27 to permit urine access to the material of the island 16.

For further details of the construction of the panel 18 and the rectangular extension 22, reference may be had to my aforesaid pending application wherein the fan shaped panel portion is similar in construction, and the rectangular extension differs in that in my pending application the bottom of the depressed section is continuous and without perforations or apertures therein such that such extended portion can serve with an overlying cover as a container for collecting urine.

While not shown in the drawings of the present application, the inserted panel structure 18 may be secured in position relative to the top sheet 11 of the diaper 10 by means of an adhesive stripe under the fan shaped portion 18.

Instead of employing a separate panel as shown in the embodiment of FIGS. 1 to 3, the impervious barrier over the top sheet can be provided as shown in FIG. 4 by applying within the region 30 a coating material capable of sealing the pores of the porous top sheet 11. Any suitable biologically safe material may be employed for this purpose. For example, the coating may be produced by spraying a solution of polyvinyl chloride in a methyl ethyl keytone or tetrahydrofuran solvent vehicle. Examples of other materials are polyurethane elastomers and copolymers of polystyrene and polyisobutylene elastomers. The material can be applied by any known spraying technique or other coating procedure.

As shown in FIG. 4 the coating 30 is generally trapezoidal in configuration and extends between a point 31 at the general midpoint of the diaper up to a point 32 where it is above the genital area when the diaper is worn. If the top sheet 11 could be folded back as shown in FIG. 5, it would be seen that immediately beneath the top sheet substantially at the location of the end 31 of the coating 30 there is encountered the upper edge 33 of an island 34 of highly absorbent material such as the compressed cellulose sponge mentioned previously. In this embodiment, the island 34 is shown laminated to the upper surface of the layer 35 of more conventional absorbent material similar to the material 17 described with reference to the embodiment of FIGS. 1 to 3. Underneath the absorbent layer 35 is the usual back sheet 13 of liquid impermeable material.

It may be desirable to arrange for the edge 33 of the island 34 to extend further toward the front edge 36 of the diaper in order to slightly underly the extremity of the coating layer 30.

Instead of locating the coating layer 30 on the exterior of the top sheet 11 as shown in FIG. 4, it may be located on the underside of the top sheet (not shown) or it may be located directly on the absorbent layer 35 as shown in FIG. 6 and designated by the reference numeral 40. In all other respects, the embodiment of FIG. 6 may be similar to that of FIGS. 4 and 5.

It should be understood, of course, that the island 34 shown in the embodiments of FIGS. 4 to 6 may be shaped differently from the trapezoidal configuration and may be embedded in the surrounding absorbent material 35 rather than being laminated to an upper surface thereof.

Throughout the preceding discussion the island material has been referred to as consisting of compressed cellulose sponge. An advantage of this material is that upon wetting the sponge it tends to expand rapidly developing a suction for rapidly absorbing any liquid with which it is in contact. Thus, it tends to trap the urine that is directed to it by the panel of liquid impervious material or that might reach it directly through the overlying porous top sheet of the diaper. Obviously, the invention need not be limited to compressed cellulose sponge but can be extended to the use of any super absorbent material having similar or superior liquid absorbing properties.

Having described the subject invention with reference to the presently preferred embodiments thereof, it should be apparent to those skilled in the subject art that various changes in construction may be effected without departing from the true spirit of the invention as defined in the appended claims.

What is claimed is:

1. A disposable diaper comprising at least a layer of absorbent material having a surface intended to face the wearer and extending throughout substantially the entire diaper, said absorbent layer including an island of a first absorbent material surrounded by an expanse of a second absorbent material, where the liquid absorbing capacity per unit volume of said island material is greater than that of said surrounding expanse, said island being located in that portion of the diaper that, when the diaper is worn, places said island at the rear of the wearer extending toward the perineum region, and an expanse of liquid impermeable material overlying that portion of said second absorbent material expanse that overlies the general region of the genitalia when the diaper is worn, said expanse of impermeable material expanding from said genital region to said island for diverting and directing urine away from said second absorbent material and toward said island of material, said expanse of impermeable material being constructed to permit urine access to said island material.

2. A disposable diaper according to claim 1, characterized in that said expanse of impermeable material comprises a panel of a liquid impermeable material including at least one channel for guiding urine therealong.

3. A disposable diaper according to claim 2, wherein said diaper includes a liquid impervious backing sheet laminated to the side of said layer of absorbent material intended to be worn facing away from the wearer, and a liquid permeable top sheet laminated to the opposite side of said layer of absorbent material, characterized in that said panel is secured to the exposed surface of said top sheet.

4. A disposable diaper according to claim 1, wherein said diaper includes a liquid impervious backing sheet laminated to the side of said layer of absorbent material intended to be worn facing away from the wearer, and a liquid permeable top sheet laminated to the opposite side of said layer of absorbent material, characterized in that said expanse of impermeable material comprises a coating layer of a liquid impermeable material on a surface of said top sheet.

5. A disposable diaper according to claim 1, wherein said diaper includes a liquid impervious backing sheet laminated to the side of said layer of absorbent material intended to be worn facing away from the wearer, and a liquid permeable top sheet laminated to the opposite side of said layer of absorbent material, characterized in that said expanse of impermeable material comprises a coating layer of a liquid impermeable material on said opposite side of said layer of absorbent material beneath said top sheet.

6. A disposable diaper according to claim 5, characterized in that said expanse of a second absorbent material comprises a non-woven wadding of highly absorbent essentially hydrophilic fiber aggregates.

7. A disposable diaper according to claim 3, characterized in that said expanse of a second absorbent material comprises a non-woven wadding of highly absorbent essentially hydrophilic fiber aggregates.

8. A disposable diaper according to claim 4, characterized in that said expanse of a second absorbent material comprises a non-woven wadding of highly absorbent essentially hydrophilic fiber aggregates.

9. A disposable diaper comprising a laminated assembly of a liquid impervious backing sheet, an absorbent core, and a liquid permeable top sheet, characterized in that a region of said top sheet extending from the crotch area of said diaper toward the front top edge a distance sufficient to overlie the genital region when worn and of sufficient width to divert and direct urine toward the crotch area, is provided with a liquid impermeable barrier, and over a zone commencing approximately where said barrier terminates in the crotch area and extending in the opposite direction part way to the rear top edge, said absorbent core is provided with greater absorbency than the remainder of said core.

10. A disposable diaper according to claim 9, characterized in that said zone of greater absorbency is provided by a body of highly compressed cellulose sponge that expands rapidly in the presence of liquid thereby developing a suction for rapidly absorbing said liquid.

11. A disposable diaper according to claim 10, characterized in that said barrier comprises a panel of a liquid impermeable material including at least one channel for guiding urine therealong, said panel being secured to the exposed surface of said top sheet.

12. A disposable diaper according to claim 10, characterized in that said barrier comprises a coating layer of a liquid impermeable material on a surface of said top sheet.

13. A disposable diaper according to claim 10, characterized in that said barrier comprises a coating layer of a liquid impermeable material on said absorbent core facing said top sheet.

14. A disposable diaper according to claim 9, characterized in that said barrier comprises a panel of a liquid impermeable material including at least one channel for guiding urine therealong, said panel being secured to the exposed surface of said top sheet.

15. A disposable diaper according to claim 9, characterized in that said barrier comprises a coating layer of a liquid impermeable material on a surface of said top sheet.

16. A disposable diaper according to claim 9, characterized in that said barrier comprises a coating layer of a liquid impermeable material on said absorbent core facing said top sheet.

17. A disposable diaper comprising at least an expanse of absorbent material having a surface intended to face the wearer and extending throughout substantially the entire diaper, said absorbent expanse including an island of a first absorbent material surrounded at least in directions parallel to said surface by an expanse of a second absorbent material, where the liquid absorbing capacity per unit volume of said island material is greater than that of said surrounding expanse, said island being located in that portion of the diaper that, when the diaper is worn, places said island at the rear of the wearer extending toward the perineum region, and an expanse of liquid impermeable material overlying that portion of said second absorbent material expanse that overlies the general region of the genitalia when the diaper is worn, said expanse of impermeable material extending from said genital region to said island for diverting and directing urine away from said second absorbent material and toward said island of material, said expanse of impermeable material being constructed to permit urine access to said island material.

18. A disposable diaper according to claim 17, characterized in that said first absorbent material has a surface area of at least 12.5 in$^2$.

19. A disposable diaper according to claim 18, characterized in that said first absorbent material has the capacity to absorb at least 50 cc. of urine.

20. A disposable diaper according to claim 18, characterized in that said island comprises a body of highly compressed cellulose sponge that expands rapidly in the presence of liquid thereby developing a suction for rapidly absorbing said liquid.

21. A disposable diaper according to claim 20, characterized in that said body of compressed sponge has a compressed volume of approximately 7 in$^3$, and is expandable to a volume of approximately 35 in$^3$ when completely wetted and relaxed.

22. A disposable diaper according to claim 17, characterized in that said second material has a surface that is intended to face the wearer, and said island of material is in the form of a layer laminated to said surface of said second material.

23. A disposable diaper comprising at least an expanse of absorbent material having a surface intended to face the wearer and exending throughout substantially the entire diaper, said absorbent expanse including a centralized zone of absorbent material surrounded at least in the directions parallel to said surface by an expanse of additional absorbent material, where the liquid absorbing capacity per unit volume of said zone is greater than that of said surrounding expanse, said zone being located in that portion of the diaper that, when the diaper is worn, places said zone at the rear of the wearer extending toward the perineum region, and an expanse of non-absorbent material overlying that portion of said additional absorbent material expanse that overlies the general region of the genitalia when the diaper is worn, said expanse of non-absorbent material extending at least from said genital region to said island for diverting and directing urine away from said additional absorbent material and toward said zone, said expanse of non-absorbent material being constructed to permit urine access to said zone of absorbent material.

24. A disposable diaper according to claim 23, characterized in that said zone of absorbent material has a surface area of at least 12.5 in$^2$.

25. A disposable diaper according to claim 24, characterized in that said zone of absorbent material has the capacity to absorb at least 50 cc. of urine.

26. A disposable diaper comprising at least a layer of absorbent material having a surface intended to face the wearer and extending throughout substantially the entire diaper, said absorbent layer including an island of a first absorbent material surrounded by an expanse of a second absorbent material, where the liquid absorbing capacity per unit volume of said island material is greater than that of said surrounding expanse, said island being located in that portion of the diaper that, when the diaper is worn, places said island at the rear of the wearer extending toward the perineum region, and an expanse of non-absorbent material overlying that portion of said second absorbent material expanse that overlies the general region of the genitalia when the diaper is worn, said expanse of non-absorbent material extending from said genital region to said island for diverting and directing urine away from said second absorbent material and toward said island of material, said expanse of non-absorbent material being constructed to permit urine access to said island material.

27. A disposable diaper according to claim 26, wherein said diaper includes a liquid impervious backing sheet laminated to the side of said layer of absorbent material intended to be worn facing away from the wearer, and a liquid permeable top sheet laminated to the opposite side of said layer of absorbent material, characterized in that said expanse of non-absorbent material comprises a coating layer of a liquid impermeable material on a surface of said top sheet.

* * * * *

UNITED STATES PATENT AND TRADEMARK OFFICE
CERTIFICATE OF CORRECTION

PATENT NO. : 4,778,459
DATED : October 18, 1988
INVENTOR(S) : RICHARD C. FUISZ

It is certified that error appears in the above-identified patent and that said Letters Patent is hereby corrected as shown below:

Column 5, line 23, "expanding" should read --extending--.

Signed and Sealed this

Ninth Day of May, 1989

Attest:

DONALD J. QUIGG

Attesting Officer

Commissioner of Patents and Trademarks